(12) United States Patent
Kim et al.

(10) Patent No.: US 11,361,938 B2
(45) Date of Patent: Jun. 14, 2022

(54) PLASMA ENHANCEMENT MEMBER, AND PLASMA SUPPLYING APPARATUS AND MEDICAL INSTRUMENT INCLUDING THE SAME

(71) Applicant: FEAGLE CO., LTD, Yangsan-si (KR)

(72) Inventors: Youngmin Kim, Gimhae-si (KR); Jeonghae Choi, Busan (KR); Seeun Yun, Busan (KR)

(73) Assignee: FEAGLE CO., LTD, Yangsan-si (KR)

( * ) Notice: Subject to any disclaimer, the term of this patent is extended or adjusted under 35 U.S.C. 154(b) by 183 days.

(21) Appl. No.: 15/527,714

(22) PCT Filed: Aug. 2, 2016

(86) PCT No.: PCT/KR2016/008481
§ 371 (c)(1),
(2) Date: May 18, 2017

(87) PCT Pub. No.: WO2018/026026
PCT Pub. Date: Feb. 8, 2018

(65) Prior Publication Data
US 2018/0366298 A1    Dec. 20, 2018

(51) Int. Cl.
*H01J 37/32* (2006.01)
*A61L 2/14* (2006.01)
(Continued)

(52) U.S. Cl.
CPC ...... *H01J 37/32009* (2013.01); *A61C 19/066* (2013.01); *A61L 2/0011* (2013.01);
(Continued)

(58) Field of Classification Search
CPC ..... A61C 19/06; A61C 19/063; A61C 19/066; A61C 3/00; H05H 2240/20;
(Continued)

(56) References Cited

U.S. PATENT DOCUMENTS 5,667,753 A * 9/1997 Jacobs .................... A61L 2/208
                                                            422/29
5,785,934 A * 7/1998 Jacobs .................... C01B 15/16
                                                            422/29
(Continued)

FOREIGN PATENT DOCUMENTS

JP    2001-068298 A    3/2001
JP    2001-340363 A    11/2001
(Continued)

OTHER PUBLICATIONS

International Search Report in International Application No. PCT/KR2016/008481, dated Apr. 20, 2017.

*Primary Examiner* — Edward Moran
*Assistant Examiner* — Matthew P Saunders
(74) *Attorney, Agent, or Firm* — Park, Kim & Suh, LLC

(57) ABSTRACT

Disclosed are to a plasma enhancement member, and a plasma supplying apparatus and a medical instrument including the same. The plasma enhancement member includes a coupling part coupled to an apparatus for generating plasma, an enhancement material accommodating part configured to accommodate an enhancement material for enhancing an operation of the plasma, and a plasma discharge part configured to discharge the plasma including the enhancement material.

10 Claims, 24 Drawing Sheets

(51) Int. Cl.
   *A61L 2/00* (2006.01)
   *A61C 19/06* (2006.01)
   *A61N 1/44* (2006.01)
   *A61C 3/00* (2006.01)
   *H05H 1/24* (2006.01)

(52) U.S. Cl.
   CPC .............. *A61L 2/14* (2013.01); *A61N 1/44* (2013.01); *H05H 1/2406* (2013.01); *A61C 3/00* (2013.01); *A61L 2202/11* (2013.01); *A61L 2202/15* (2013.01); *A61L 2202/16* (2013.01); *H05H 2245/30* (2021.05)

(58) Field of Classification Search
   CPC .. H05H 2277/10; H05H 2245/30; H05H 1/42; H05H 1/2406; A61N 1/44; A61N 2005/0606; A61N 2005/0644; A61B 18/042; A61L 2/208; A61L 9/22; A61L 2/0011; A61L 2/14; A61L 2202/11; A61L 2202/15; A61L 2202/16; H01J 37/32009
   See application file for complete search history.

(56) References Cited

U.S. PATENT DOCUMENTS

| | | | | |
|---|---|---|---|---|
| 5,876,663 | A * | 3/1999 | Laroussi | A23L 3/005 204/164 |
| 6,790,410 | B2 * | 9/2004 | Metzner | A61L 2/0011 422/186.23 |
| 7,156,656 | B2 * | 1/2007 | Duret | A61C 19/066 433/215 |
| 8,994,270 | B2 * | 3/2015 | Koo | H01J 37/32577 315/111.21 |
| 9,117,636 | B2 * | 8/2015 | Koo | H01J 37/32532 |
| 9,192,776 | B2 | 11/2015 | Hummel et al. | |
| 9,287,091 | B2 * | 3/2016 | Koo | H01J 37/32449 |
| 2005/0064371 | A1 * | 3/2005 | Soukos | A61N 5/0601 433/217.1 |
| 2005/0221251 | A1 * | 10/2005 | Soukos | A61N 5/0601 433/29 |
| 2008/0254405 | A1 * | 10/2008 | Montgomery | A61C 19/06 433/29 |
| 2010/0130911 | A1 | 5/2010 | Morfill | |
| 2010/0209293 | A1 * | 8/2010 | Ikawa | C02F 1/30 422/22 |
| 2011/0101862 | A1 * | 5/2011 | Koo | H01J 37/32449 315/111.21 |
| 2011/0183284 | A1 * | 7/2011 | Yamanaka | A61C 17/02 433/32 |
| 2012/0107761 | A1 | 5/2012 | Holbeche | |
| 2013/0059273 | A1 * | 3/2013 | Koo | A61C 19/066 433/216 |
| 2013/0062014 | A1 * | 3/2013 | Koo | A61C 19/00 156/345.11 |
| 2013/0068732 | A1 * | 3/2013 | Watson | A61L 2/0094 219/121.5 |
| 2013/0116682 | A1 * | 5/2013 | Koo | B05D 1/62 606/41 |
| 2014/0188071 | A1 * | 7/2014 | Jacofsky | A61N 1/44 604/501 |
| 2014/0225495 | A1 * | 8/2014 | Koo | H05H 1/28 313/13 |
| 2015/0111170 | A1 * | 4/2015 | Guy, Sr. | A61C 5/62 433/89 |
| 2015/0200076 | A1 * | 7/2015 | Koo | H05H 1/2406 315/111.21 |
| 2015/0327963 | A1 * | 11/2015 | Fregoso | A61C 3/00 433/29 |
| 2016/0106993 | A1 * | 4/2016 | Watson | H01J 37/32825 604/24 |
| 2016/0135657 | A1 * | 5/2016 | Mao | A47L 13/17 433/89 |

FOREIGN PATENT DOCUMENTS

| | | | | |
|---|---|---|---|---|
| KR | 10-2010-0058715 A | | 6/2010 | |
| KR | 20100058715 A | * | 6/2010 | ........... A61C 19/066 |
| KR | 10-1147397 B1 | | 5/2012 | |
| KR | 10-1171094 B1 | | 8/2012 | |
| KR | 10-2012-0135128 A | | 12/2012 | |
| KR | 10-2012-0135129 A | | 12/2012 | |
| WO | 2010/138103 A1 | | 12/2010 | |
| WO | 2011/061477 A1 | | 5/2011 | |
| WO | 2015/083155 A1 | | 6/2015 | |

* cited by examiner

Straight pipe    Curved pipe 1    Curved pipe 2    Bent pipe 1    Bent pipe 2

Enhancement material
+
Plasma

Enhancement material
+
Plasma

| Plasma ejection time(s) | 15 | 30 | 60 |
|---|---|---|---|
| Comparison example |  |  |  |
| Embodiment |  |  |  |

Comparison example

| | Before whitening process | After whitening process |
|---|---|---|
| Tooth 1 |  |  |
| Tooth 2 |  |  |

Embodiment

| | Before whitening process | After whitening process |
|---|---|---|
| Tooth 1 |  |  |
| Tooth 2 |  |  |

PLASMA ENHANCEMENT MEMBER, AND PLASMA SUPPLYING APPARATUS AND MEDICAL INSTRUMENT INCLUDING THE SAME

CROSS-REFERENCE TO RELATED APPLICATIONS

This application is the National Stage filing under 35 U.S.C. 371 of International Application No. PCT/KR2016/008481, filed on Aug. 2, 2016, the contents of which are all hereby incorporated by reference herein in their entirety.

TECHNICAL FIELD

Embodiments of the inventive concept described herein relate to a plasma enhancement member, and a plasma supplying apparatus and a medical instrument including the same.

BACKGROUND

Plasma corresponds to a state in which a material is separated into electrons having a negative charge and ions having a positive charge, and the reactivity of the material is maximized in the plasma so that ionization and recoupling of the material are actively performed.

Efforts to practically and artificially generating plasma have been continuously made. In recent years, efforts to treat skin diseases such as atopy or acnes have been made. In this case, the plasma improves an affected area by removing harmful germs of skin and reproducing tissues.

However, in order that the plasma may be widely used in various medical fields, the currently known effects need to be further improved and the treatment effect of the plasma need to be maximized.

SUMMARY

Technical Problem

Embodiments of the inventive concept provide provides a plasma enhancement member that may maximize an effect of plasma by enhancing an operation of the plasma, a plasma supplying apparatus, and a medical instrument.

Technical Solution

In accordance with an aspect of the inventive concept, there is provided a plasma enhancement member including a coupling part coupled to an apparatus for generating plasma, an enhancement material accommodating part configured to accommodate an enhancement material for enhancing an operation of the plasma, and a plasma discharge part configured to discharge the plasma including the enhancement material.

The coupling part may be coupled to a nozzle, through which the plasma is discharged from the apparatus.

The coupling part may be screw-coupled to the nozzle.

The coupling part may be coupled to a screw formed in the nozzle to have a pitch in a direction that is parallel to an axis of the nozzle.

The enhancement material accommodating part may be formed in the interior of the plasma enhancement member to accommodate the enhancement material in a space formed on a delivery path, along which plasma is delivered from the apparatus to the plasma discharge part.

The enhancement material accommodating part may be formed in the interior of the plasma enhancement member to accommodate the enhancement material on a delivery path, along which plasma is delivered from the apparatus to the plasma discharge part.

The delivery path may include a straight pipe extending from the nozzle in a linear form.

The delivery path may include a curved pipe extending from the nozzle in a curved form.

The curved pipe may extend on a virtual plane on which the nozzle and the plasma discharge part are located.

The curved pipe may be wound around a virtual line connecting the nozzle and the plasma discharge part.

The delivery path may include a bent pipe extending from the nozzle in a bent form.

The bent pipe may extend on a virtual plane on which the nozzle and the plasma discharge part are located.

The bent pipe may be wound around a virtual line connecting the nozzle and the plasma discharge part.

The enhancement material accommodating part may include a cavity configured to accommodate the enhancement material at a location corresponding to an apex of the bent pipe.

In accordance with another aspect of the inventive concept, there is provided a plasma supplying apparatus including a power source unit configured to supply electric power for generating plasma, a power discharge unit configured to generate plasma by receiving electric power and discharging the electric power from gas, and a plasma enhancement unit configured to enhance an operation of plasma, wherein the plasma enhancement unit includes a coupling part coupled to the power discharge unit, an enhancement material accommodating part configured to accommodate an enhancement material for enhancing an operation of the plasma, and a plasma discharge part configured to discharge the plasma including the enhancement material.

In accordance with another aspect of the inventive concept, there is provided a medical instrument including a power source unit configured to supply electric power for generating plasma, a power discharge unit configured to generate plasma by receiving electric power and discharging the electric power from gas, a plasma enhancement unit configured to enhance an operation of plasma, and a body interface unit formed in the plasma enhancement unit to interact with a human body, wherein the plasma enhancement unit includes a coupling part coupled to the power discharge unit, an enhancement material accommodating part configured to accommodate an enhancement material for enhancing an operation of the plasma, and a plasma discharge part configured to discharge the plasma including the enhancement material.

The enhancement material accommodating unit may accommodate hydrogen peroxide as the enhancement material.

The body interface unit may include a periodontal separation unit protruding from the plasma enhancement unit in a direction that is perpendicular to a discharge direction of plasma to secure a gap between a tooth and a periodontal part.

The body interface unit may include a cover extending from the plasma discharge part to surround a space from which the plasma is discharged.

A section of the cover viewed from a first direction that is perpendicular to the discharge direction of plasma may be curved and a section of the cover viewed from a second direction that is perpendicular to the discharge direction of the plasma and the first direction may be straight.

An area of a section of the cover, which section is perpendicular to the discharge direction of the plasma, may increase as it goes away from the plasma discharge part.

The cover may accommodate the enhancement material therein.

Advantageous Effects

According to an embodiment of the inventive concept, even only by attaching the enhancement member to the apparatus for generating the plasma, the effect of using the plasma may be maximized through enhancing the action caused by the plasma. In particular, various therapeutic effects including the plasma sterilization effect may be greatly improved by appropriately selecting the enhancement material provided in the plasma enhancement member.

DETAILED DESCRIPTION

The above and other aspects, features and advantages of the invention will become apparent from the following description of the following embodiments given in conjunction with the accompanying drawings. However, the inventive concept is not limited to the embodiments disclosed below, but may be implemented in various forms. The embodiments of the inventive concept is provided to make the disclosure of the inventive concept complete and fully inform those skilled in the art to which the inventive concept pertains of the scope of the inventive concept.

Although not defined, all the terms (including technical or scientific terms) used herein may have the same meanings that are generally accepted by the common technologies in the field to which the inventive concept pertains. The terms defined by the general dictionaries may be construed to having the same meanings as those meant in the related technologies and/or the disclosure of the application, and will neither become conceptual nor be construed to be excessively formal even though not clearly defined herein.

The terms used herein are provided to describe the embodiments but not to limit the inventive concept. In the specification, the singular forms include plural forms unless particularly mentioned. The expressions 'include' and/or its various conjugated forms, such as 'including', which are used in the specification do not exclude existence or addition of one or more compositions, substances, elements, steps, operations, and/or devices. In the specification, the term 'and/or' represents enumerated configurations or various combinations thereof.

Hereinafter, exemplary embodiments of the inventive concept will be described in detail with reference to the accompanying drawings.

Figure 1:
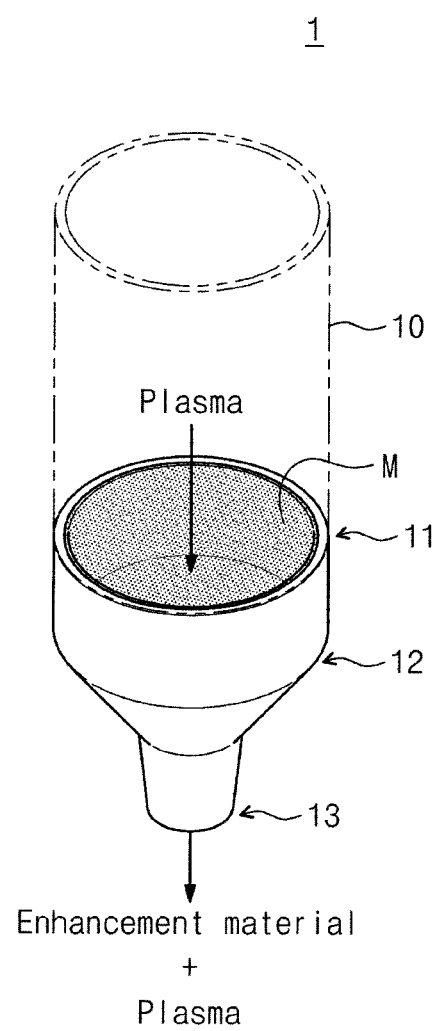
FIGS. 1 and 2 are an exemplary perspective view and a sectional view of a plasma enhancement member according to an embodiment of the inventive concept.
Figure 2:
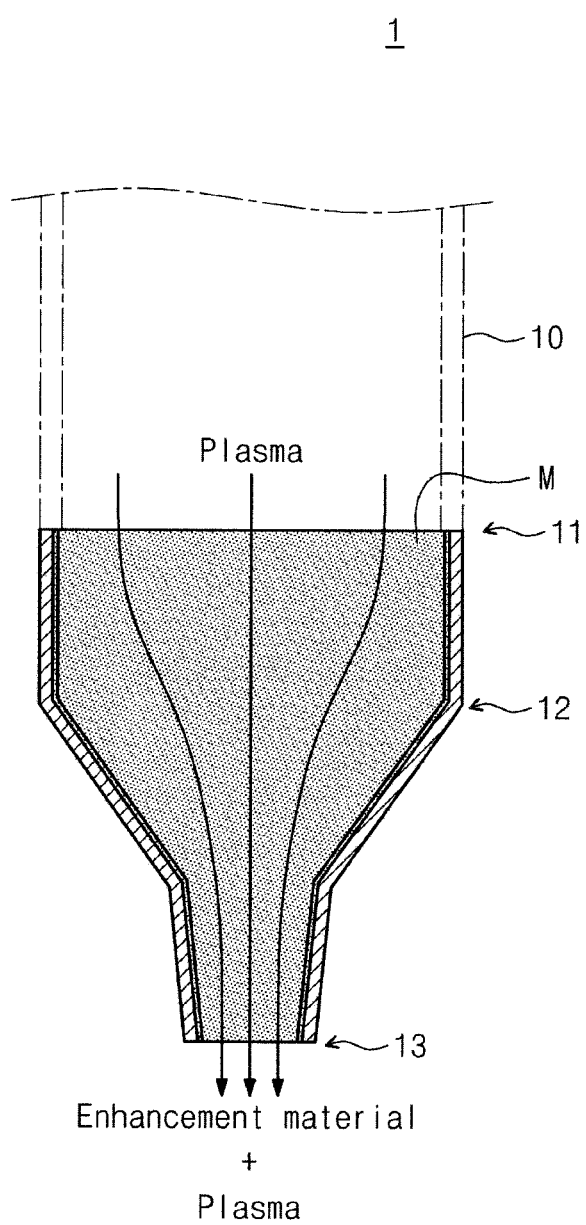

FIGS. 1 and 2 are an exemplary perspective view and a sectional view of a plasma enhancement member 1 according to an embodiment of the inventive concept.

The plasma enhancement member 1 according to the embodiment of the inventive concept is a member attached to an apparatus for generating plasma to enhance a unique operation of plasma, and includes an enhancement material M for enhancing an operation of plasma at a location by which the plasma passes to provide plasma mixed with the enhancement material M.

Referring to FIGS. 1 and 2, the plasma enhancement member 1 includes a coupling part 11 coupled to the apparatus 10 for generating plasma, an enhancement material accommodating part 12 configured to accommodate an enhancement material M for enhancing an operation of plasma, and a plasma discharge part 13 configured to discharge plasma including the enhancement material M.

The coupling part 11 may be coupled to a nozzle 9 through which plasma is discharged from the plasma generating apparatus 10. As the coupling part 11 is coupled to an end of the nozzle 9 of the plasma generating apparatus 10, the plasma generated by the apparatus 10 is discharged together with the enhancement material M via the plasma enhancement member 1.

Figure 3:
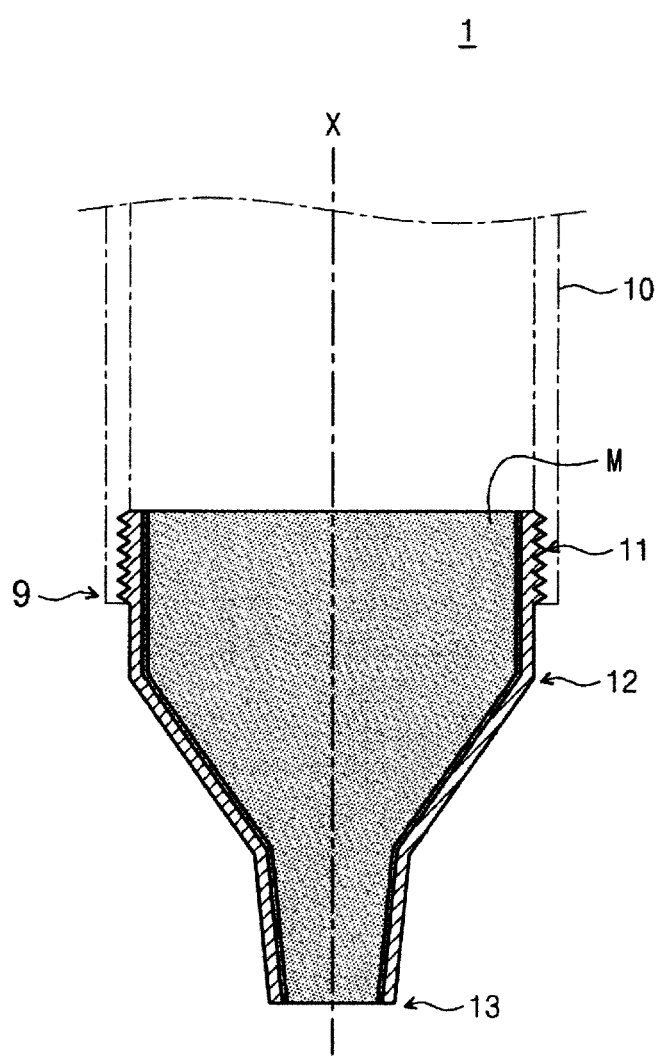
FIGS. 3 and 4 are an exemplary sectional view and a side view of a plasma enhancement member according to an embodiment of the inventive concept.
Figure 4:
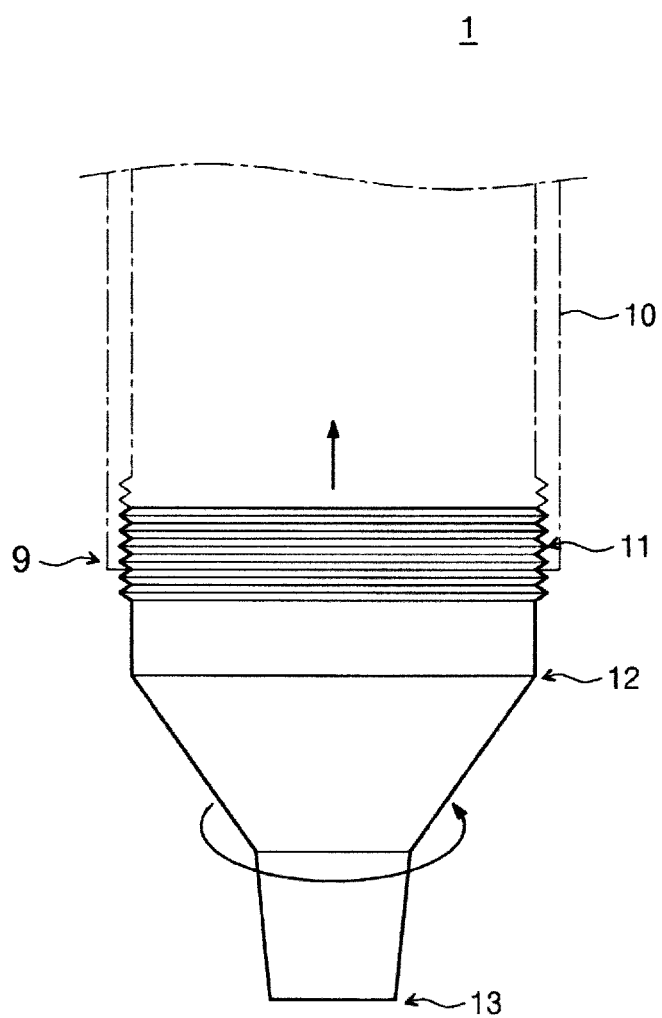

FIGS. 3 and 4 are an exemplary sectional view and a side view of a plasma enhancement member 1 according to an embodiment of the inventive concept.

According to the embodiment of the inventive concept, the coupling part 11 may be screw-coupled to the nozzle 9 of the apparatus 10. As illustrated in FIG. 3, in order to screw-couple the coupling part 11 and the nozzle 9 of the apparatus 10, screw threads that may be engaged with each other are formed in the nozzle 9 and the coupling part 11.

Moreover, according to the embodiment, the coupling part 11 may be coupled to a screw formed in the nozzle 9 to have a pitch in a direction that is parallel to the axis X of the nozzle 9. In other words, the pitch of the screw formed in the nozzle 9 as illustrated in FIG. 3 may extend in the direction of the axis X of the nozzle 9.

Due to the structure, as illustrated in FIG. 4, a degree of protrusion of the plasma enhancement member 1 may be adjusted by rotating the plasma enhancement member 1 about the axis X of the nozzle. According to the embodiment, when a length of the plasma jet discharged from a plasma discharge part 13 of the plasma enhancement member 1 is limited and a distance between a target portion (for example, an affected area) to which plasma is applied and the plasma enhance member 1 is not constant, the user may apply plasma more effectively to the target portion by adjusting the degree of protrusion of the plasma enhancement member 1, which faces the target portion.

The enhancement material accommodating part 12 accommodates an enhancement material M for enhancing an operation of the plasma.

For example, as illustrated in FIGS. 1 to 3, the enhancement material M may be applied to an inner surface of the enhancement material accommodating part 12 so that the plasma and the enhancement material M passing through the enhancement accommodating part 12 may be mixed with each other.

Figure 5:
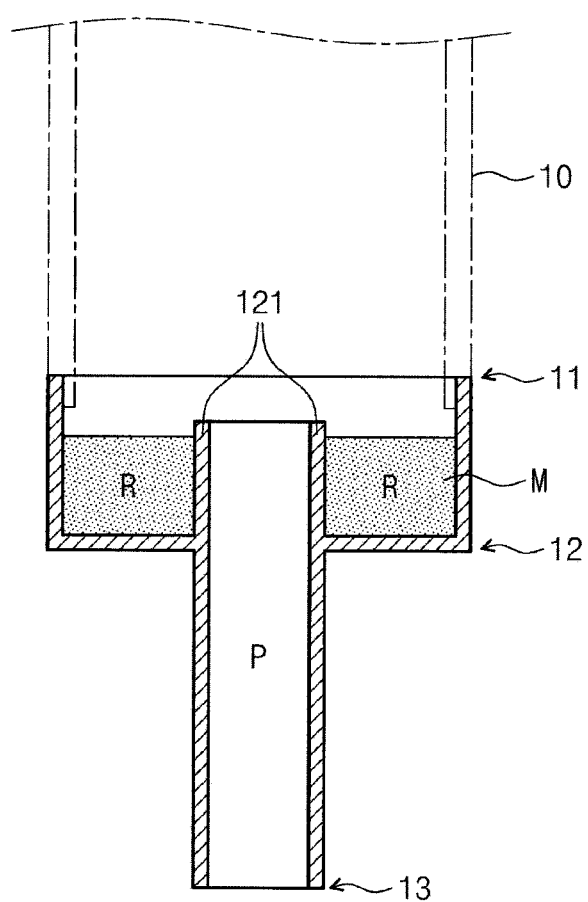
FIGS. 5 to 7 are exemplary sectional views illustrating appearances of the enhancement material accommodating part and the enhancement material accommodated in the enhancement material accommodating part according to different embodiments of the inventive concept.
Figure 6:
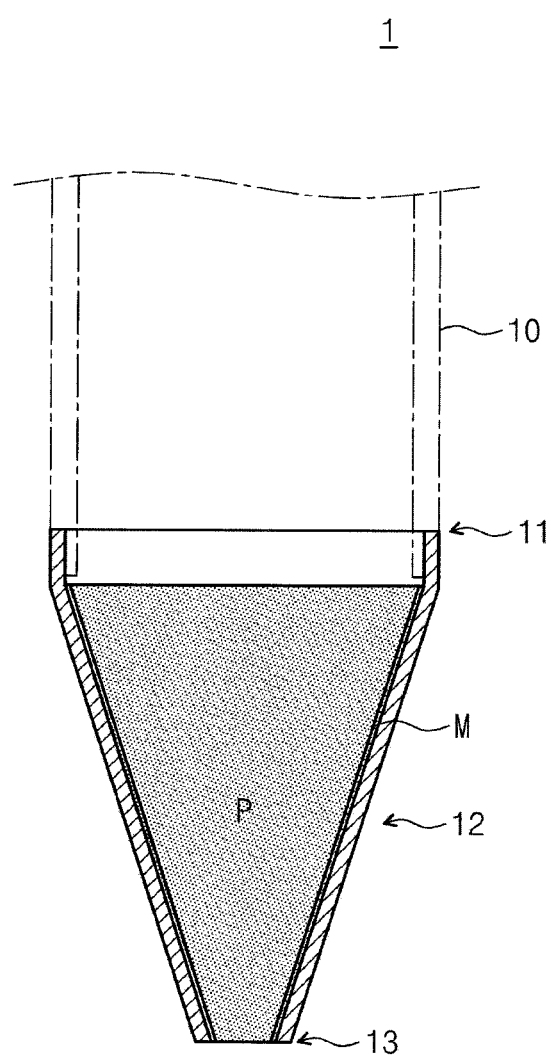
Figure 7:
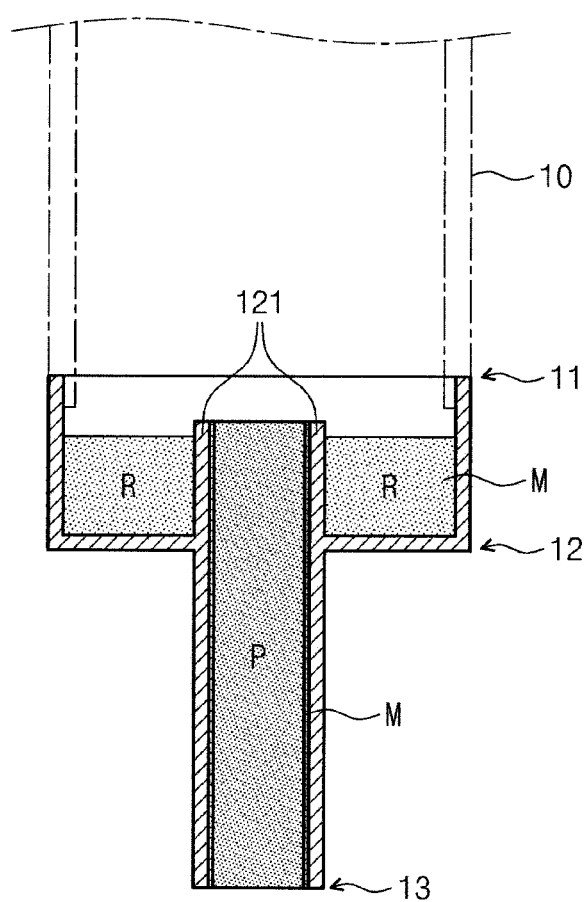

FIGS. 5 to 7 are exemplary sectional views illustrating appearances of the enhancement material accommodating part 12 and the enhancement material M accommodated in the enhancement material accommodating part 12 according to different embodiments of the inventive concept.

According to an embodiment of the inventive concept, the enhancement material accommodating part 12 may formed in the interior of the plasma enhancement member 1 to accommodate the enhancement material M in a space R formed on a delivery path P for delivering plasma from the plasma generating apparatus 10 to the plasma discharge part 13.

That is, in the embodiment, the plasma enhancement member 1 is configured to secure the space R of a specific size in the delivery path P along which the plasma passes, and the enhancement material M may be provided in the space R.

According to the embodiment, as illustrated in FIG. 5, the space R and the delivery path P may be partitioned by a partition wall 121. In this case, the enhancement material M may be accommodated between the partition wall 121 and the inner wall of the enhancement material accommodating part 12.

According to another embodiment of the inventive concept, the enhancement material accommodating part 12 may accommodate the enhancement material M on a delivery path P formed in the interior of the plasma enhancement member 1 to deliver plasma from the plasma generating apparatus 10 to the plasma discharge part 13.

For example, referring to FIG. 6, the plasma enhancement member 1 may have a tapered shape that becomes slimmer as it goes towards a tip end thereof, and the enhancement material M may be applied on a surface of the delivery path P formed in the interior of the plasma enhancement member 1.

Further, according to another embodiment of the inventive concept, the enhancement material accommodating part 12 may accommodate the enhancement material M on the delivery path P and the space R formed on the delivery path.

For example, referring to FIG. 7, the plasma enhancement member 1 may be configured to have both the delivery path P and the space R, and the enhancement material M may be both filled in the space R and coated on the delivery path P.

According to the embodiment of the inventive concept, the enhancement material accommodating part 12 may accommodate hydrogen peroxide as the enhancement material M. As can be seen from a plasma sterilization experiment and a tooth whitening experiment, which will be described below, when hydrogen peroxide of a predetermined concentration is used as the enhancement material M, the sterilization operation and the whitening operation of the plasma may be enhanced as compared with a comparison example in which only plasma is used. However, the enhancement material M is not limited to hydrogen peroxide, but various materials may be used according to a purpose of treatment and a portion for treatment.

According to the embodiment of the inventive concept, the delivery path P may include a straight pipe extending from the nozzle in a linear form. For example, in FIGS. 5 and 7, the delivery path P is a straight pipe in a linear form having a specific diameter, and in FIG. 6, the delivery path P is a straight pipe in a linear form having a variable diameter in a lengthwise direction thereof.

However, according to the embodiment, the delivery path P may include a curved pipe in a curved form or a bent pipe in a bent form in addition to the straight pipe.

Figure 8:
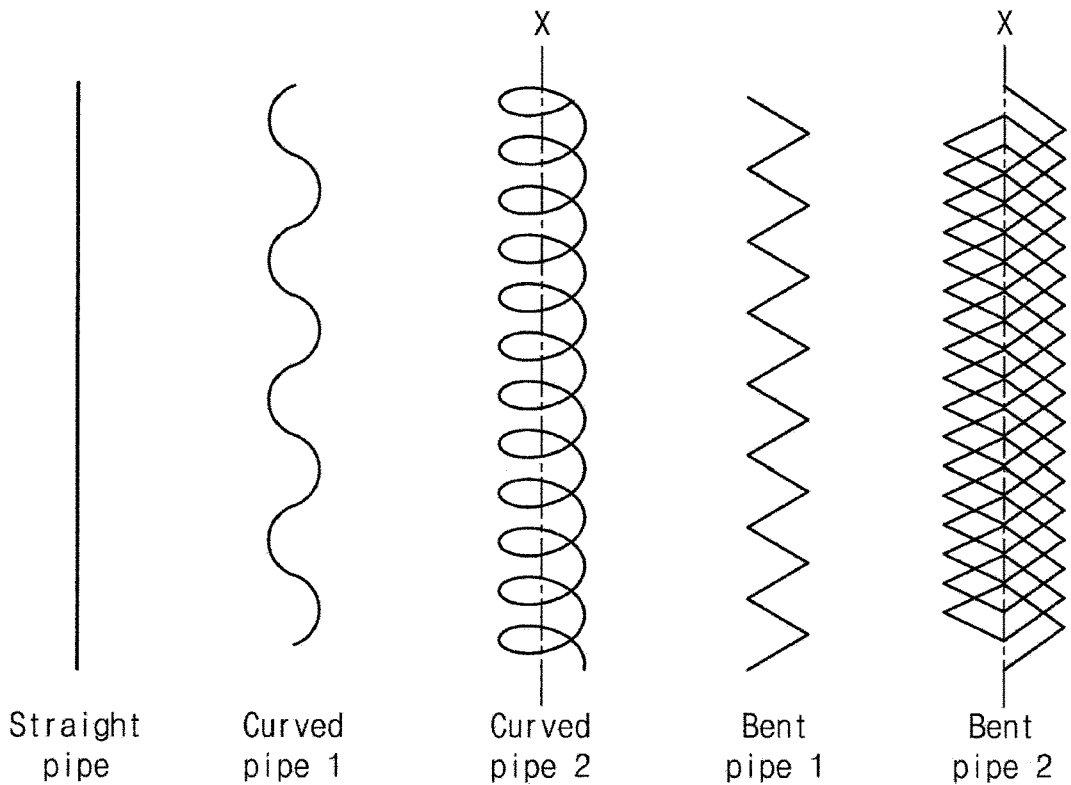
FIG. 8 is an exemplary view illustrating a schematic appearance of the delivery path formed according to various embodiments of the inventive concept.

FIG. 8 is an exemplary view illustrating a schematic appearance of the delivery path P formed according to various embodiments of the inventive concept.

FIG. 8 illustrates the delivery path P formed in the plasma enhancement member 1 while the thickness of the delivery path P is ignored and simplified by a solid line.

As described above, the delivery path P may extend from the nozzle of the plasma generating apparatus 10 to the plasma discharge part 13 of the plasma enhancement member 1 in a linear form (see the straight pipe of FIG. 8).

However, according to another embodiment, the delivery path P may extend from the nozzle to the plasma discharge part 13 in a curved form (see curved pipes 1 and 2 of FIG. 8).

In this case, the curved pipe may extend on a virtual plane, on which the nozzle and the plasma discharge part 13 are located, in a curved form. That is, as indicated by curved pipe 1 of FIG. 8, the curved pipe may be formed on a single plane to be curved.

In another case, the curved pipe may be formed around a virtual line connecting the nozzle and the discharge pipe 13 to be wound. That is, as indicated by curved pipe 2 of FIG. 8, the curved pipe may not be located on a single plane but may be formed to be wound about the axis X connecting the nozzle and the discharge pipe 13.

Moreover, according to another embodiment, the delivery path P may extend from the nozzle to the plasma discharge part 13 in a bent form (see bent pipes 1 and 2 of FIG. 8).

In this case, the bent pipe may extend on a virtual plane, on which the nozzle and the plasma discharge part 13 are located, in a bent form. That is, as indicated by bent pipe 1 of FIG. 8, the bent pipe may be formed on a single plane to be bent.

In another case, the bent pipe may be formed around a virtual line connecting the nozzle and the discharge pipe 13 to be wound. That is, as indicated by bent pipe 2 of FIG. 8, the bent pipe may not be located on a single plane but may be formed to be bent about the axis X connecting the nozzle and the discharge pipe 13.

Because the curved pipe and the bent pipe are curved or bent in a direction that is different from the direction of the axis X connecting the nozzle and the plasma discharge part 13 so that the length of a path, along which plasma passes, is longer than that of the straight pipe, a larger amount of plasma may be mixed with the enhancement material M on the delivery path P so that a degree of enhancement of an operation of the plasma due to mixing of the enhancement material M may be further improved.

Figure 9:
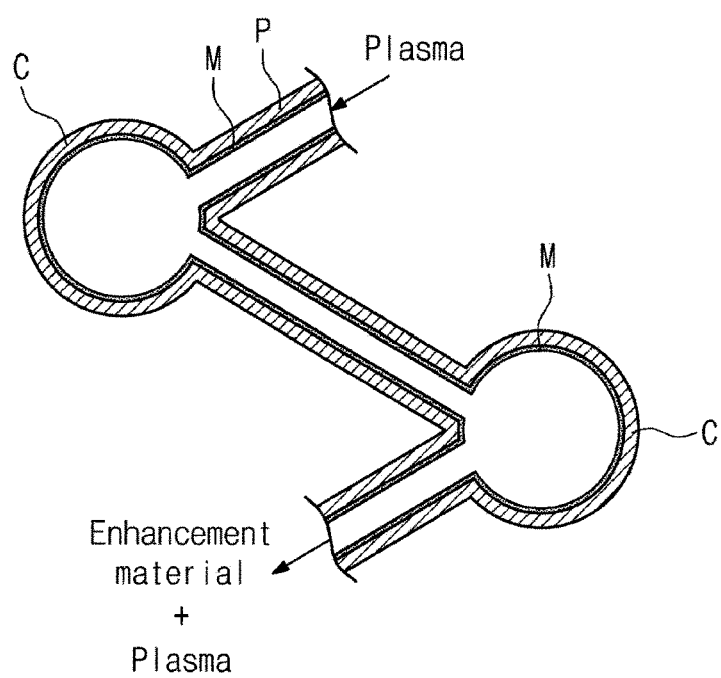
FIG. 9 is an exemplary view illustrating a delivery path and a section of a cavity formed in the delivery path P according to another embodiment of the inventive concept.

FIG. 9 is an exemplary view illustrating a delivery path P and a section of a cavity C formed in the delivery path P according to another embodiment of the inventive concept.

According to another embodiment of the inventive concept, the enhancement material accommodating part 12 may further include a cavity C for accommodating an enhancement material M at a portion corresponding to an apex of the bent pipe.

For example, as illustrated in FIG. 9, the bent pipe extending in a form of a bent line may include a cavity C at an apex at which straight pipes meet. The cavity C may be formed to have a specific volume and a specific shape and may accommodate the enhancement material M in the interior of the cavity C. As an example, although the enhancement material M may be applied to the cavity C, the inventive concept is not limited thereto and the enhancement material M may be filled on an inner surface of the cavity C.

According to the embodiment, the plasma flowing along the delivery path P enters the cavity C at a portion of the apex of the bent pipe to form a vortex in the cavity C, a larger amount of plasma may be mixed with the enhancement material M in the cavity C so that the degree of enhancement of an operation of the plasma due to mixing of the enhancement material M may be further improved.

Figure 10:
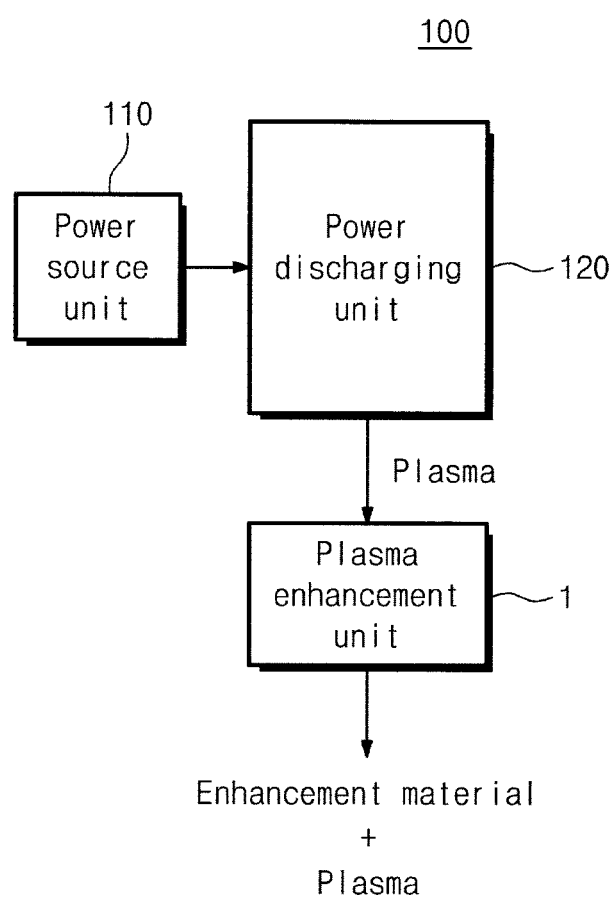
FIG. 10 is an exemplary block diagram of a plasma supplying apparatus according to an embodiment of the inventive concept.

FIG. 10 is an exemplary block diagram of a plasma supplying apparatus 100 according to an embodiment of the inventive concept.

Referring to FIG. 10, the plasma supplying apparatus 100 includes a power source unit 110, a power discharge unit 120, and a plasma enhancement unit 1.

The power source unit 110 supplies electric power for generating plasma. According to an embodiment, the power source unit 100 may supply electric power for generating plasma by providing a DC signal, but the inventive concept is not limited thereto and the power source unit 110 may provide an AC signal having a predetermined frequency.

The power discharge unit 120 generates plasma by receiving electric power from the power source unit 110 and discharging the electric power from gas. The power discharge unit 120 may separate the gas in the discharge space into electrons and ions by discharging electric power from the gas at a high voltage. The power discharge unit 120 may use air as a source gas for generating plasma. However, the source gas used by the power discharge unit 120 is not limited to air but may include an inert gas such as argon or helium.

The plasma enhancement unit 1 is a member for enhancing an operation of plasma, and corresponds to the plasma enhancement member according to the embodiment of the inventive concept.

In the plasma supplying apparatus 100 including the plasma enhancement unit 1, the plasma generated by the power discharge unit 120 is mixed with the enhancement material M included in the plasma enhancement unit 1 while passing through the plasma enhancement unit 1 and the plasma including the enhancement material M is discharged.

The plasma supplying apparatus 100 according to the embodiment of the inventive concept may be applied to a medical instrument.

In detail, the medical instrument may be constituted by further providing a body interface unit in the plasma supplying apparatus 100 including the power source unit 110, the power discharge unit 120, and the plasma enhancement unit 1.

The body interface unit is formed in the plasma enhancement unit 1 to interact with a human body.

Figure 11:
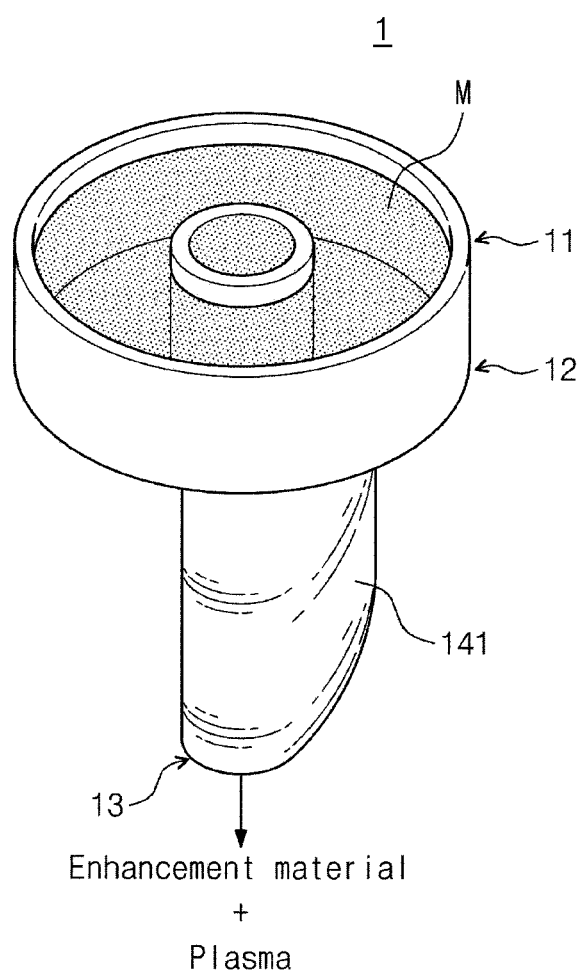
FIGS. 11 and 12 are an exemplary perspective view and a cutaway perspective view of the plasma enhancement unit provided with a periodontal separation part according to an embodiment of the inventive concept.
Figure 12:
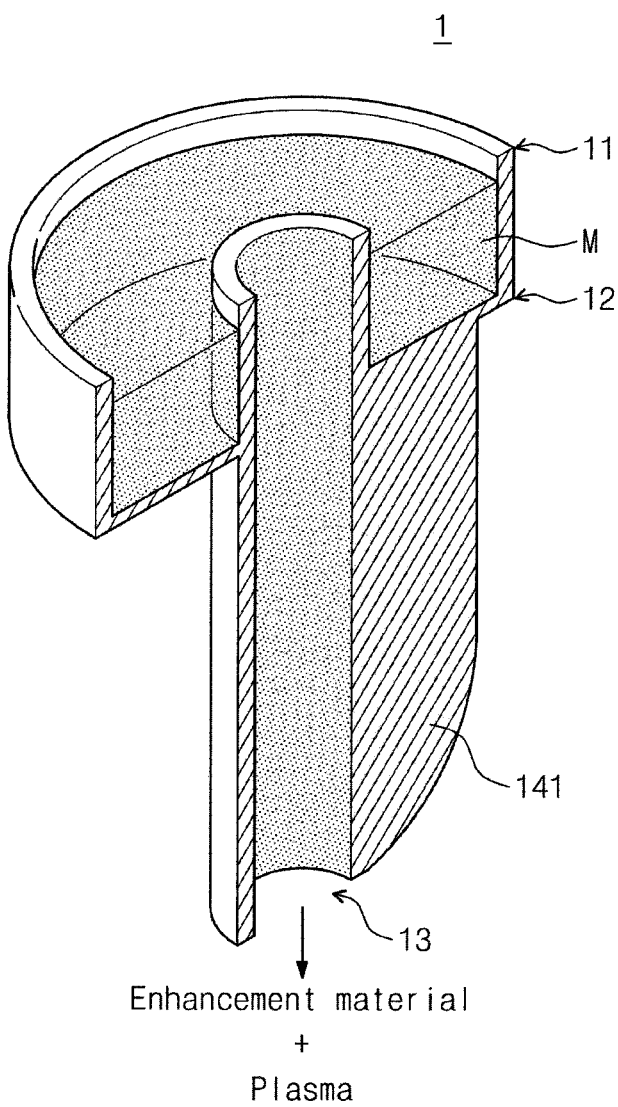

FIGS. 11 and 12 are an exemplary perspective view and a cutaway perspective view of the plasma enhancement unit 1 provided with a periodontal separation part 141 according to an embodiment of the inventive concept.

According to the embodiment of the inventive concept, the body interface unit may include a periodontal separation part 141 protruding from the plasma enhancement part unit 1 in a direction that is perpendicular to a discharge direction of the plasma to secure a gap between a tooth and a periodontal part.

As illustrated in FIGS. 11 and 12, the periodontal separation part 141 may protrude from a side surface of the plasma enhancement unit 1 in a direction that is perpendicular to the discharge direction of the plasma. As a whole, the periodontal separation part 141 may have a shape in which a blade faces a lateral side of the plasma enhancement unit 1.

Figure 13:
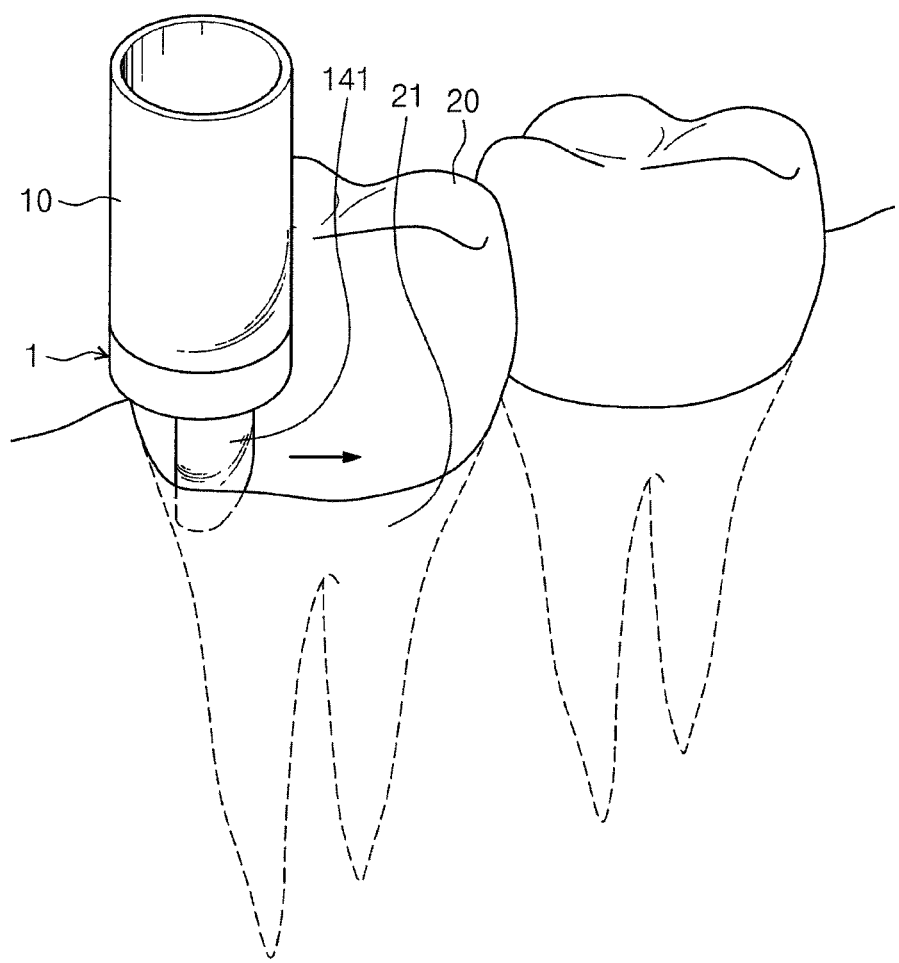
FIG. 13 is an exemplary view illustrating an appearance of treating a periodontal part by using the plasma enhancement unit provided with a periodontal separation part according to the embodiment of the inventive concept.

FIG. 13 is an exemplary view illustrating an appearance of treating a periodontal part 21 by using the plasma enhancement unit 1 provided with the periodontal separation part 141 according to an embodiment of the inventive concept.

As illustrated in FIG. 13, the user (for example, a medical staff) may insert at least portions of the plasma enhancement unit 1 and the periodontal separation part 141 between a tooth and a periodontal part 21 of the patient and supply plasma including the enhancement material M to treat or prevent inflammation generated in the periodontal part 21. Further, the user may perform a treatment on the periodontal part 21 surrounding the tooth 20 while moving the plasma enhancement unit 1 towards a direction on which the periodontal separation part 141 is provided, along a surface of the tooth 20.

Figure 14:
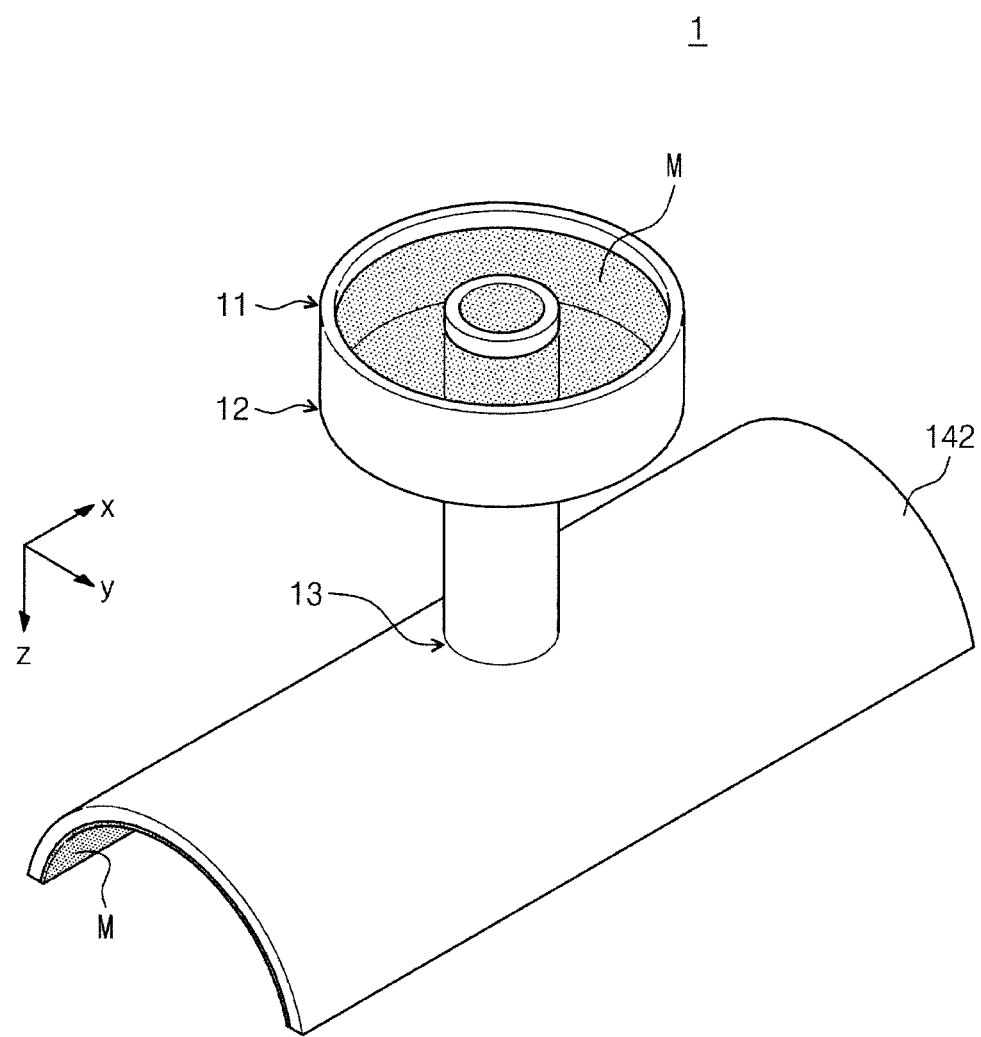
FIG. 14 is an exemplary perspective view of a plasma enhancement unit provided with a cover according to another embodiment of the inventive concept.
Figure 15:
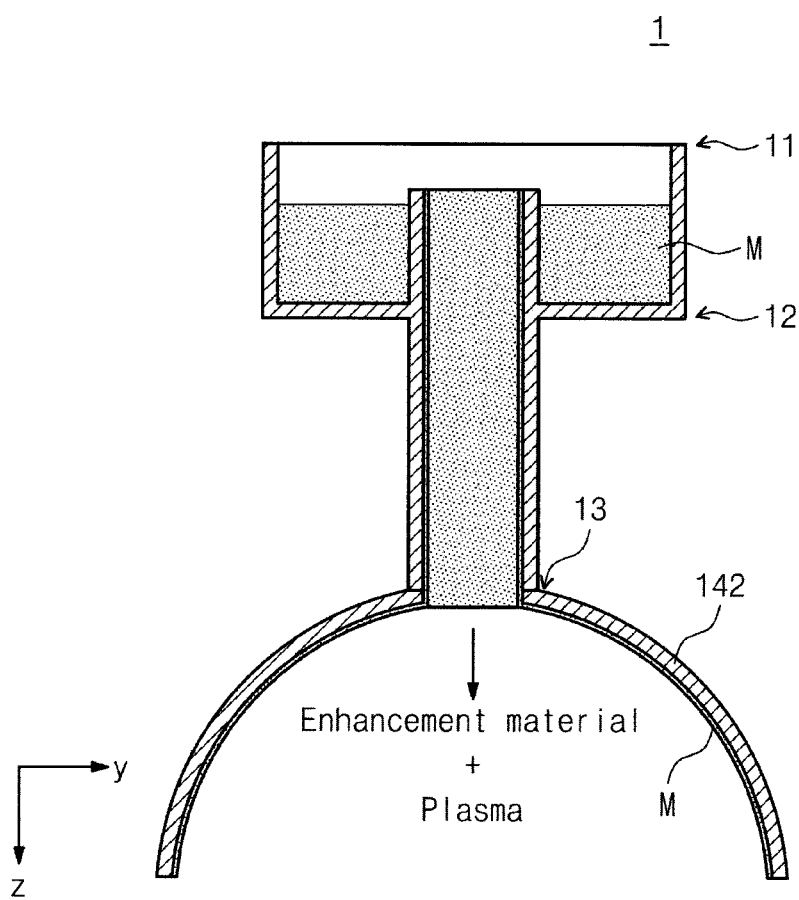
FIGS. 15 and 16 are an exemplary sectional view of the plasma enhancement unit provided with a cover according to the embodiment of the inventive concept.
Figure 16:
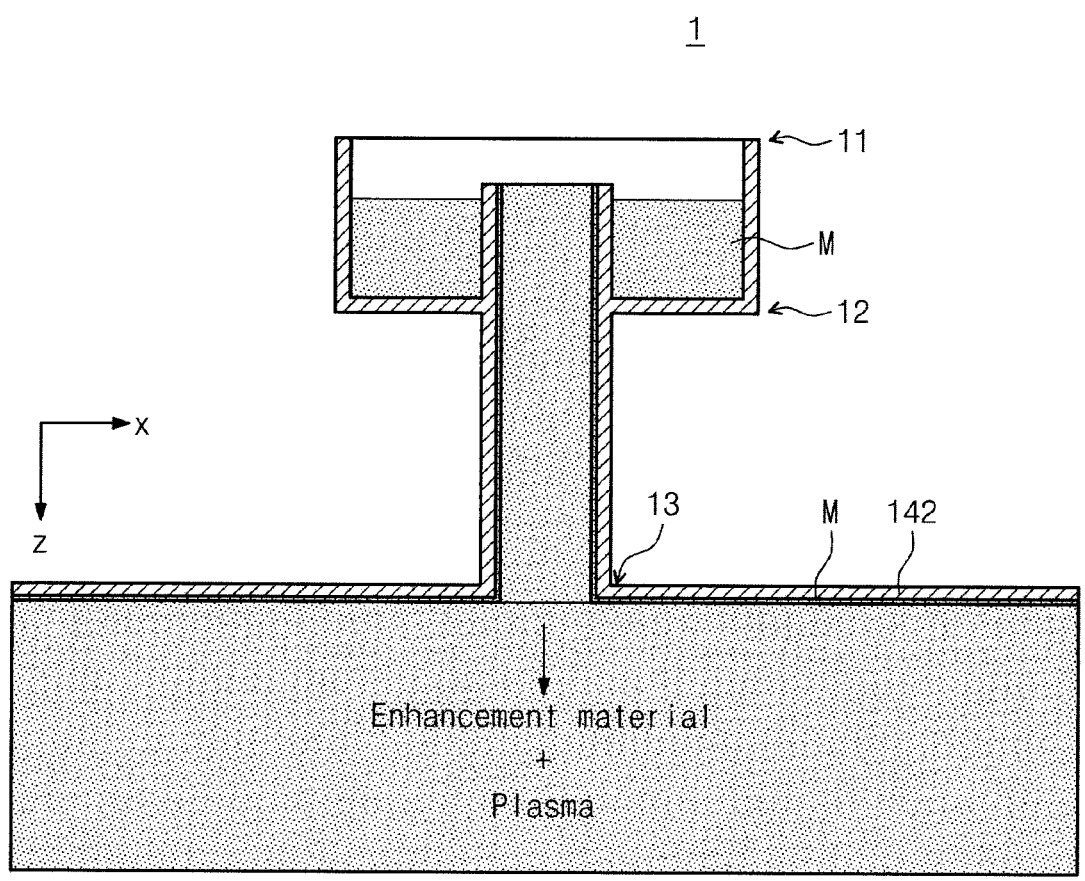

FIG. 14 is an exemplary perspective view of the plasma enhancement unit 1 provided with a cover 142 according to another embodiment of the inventive concept. FIGS. 15 and 16 are exemplary sectional views of the plasma enhancement unit 1 provided with a cover 142 according to another embodiment of the inventive concept.

According to the embodiment of the inventive concept, the body interface unit may include a cover 142 extending from the plasma discharge part 13 of the plasma enhancement unit 1 to surround a space from which plasma is discharged.

For example, as illustrated in FIGS. 14 to 16, the cover 142 may extend from the plasma discharge part 13, and a section of the cover 142 viewed from a first direction (the x-axis direction) that is perpendicular to the discharge direction of plasma may be curved (see FIG. 15) and a section of the cover 142 viewed from a second direction (the y-axis direction) that is perpendicular to the discharge direction of the plasma and the first direction may be straight (see FIG. 16).

That is, in the embodiment, the cover 142 may be straight in the first direction to have a constant section and may be curved in the second direction to have an irregular section like a portion of a side surface of a cylinder (for example, a half of the side surface of the cylinder).

Figure 17:
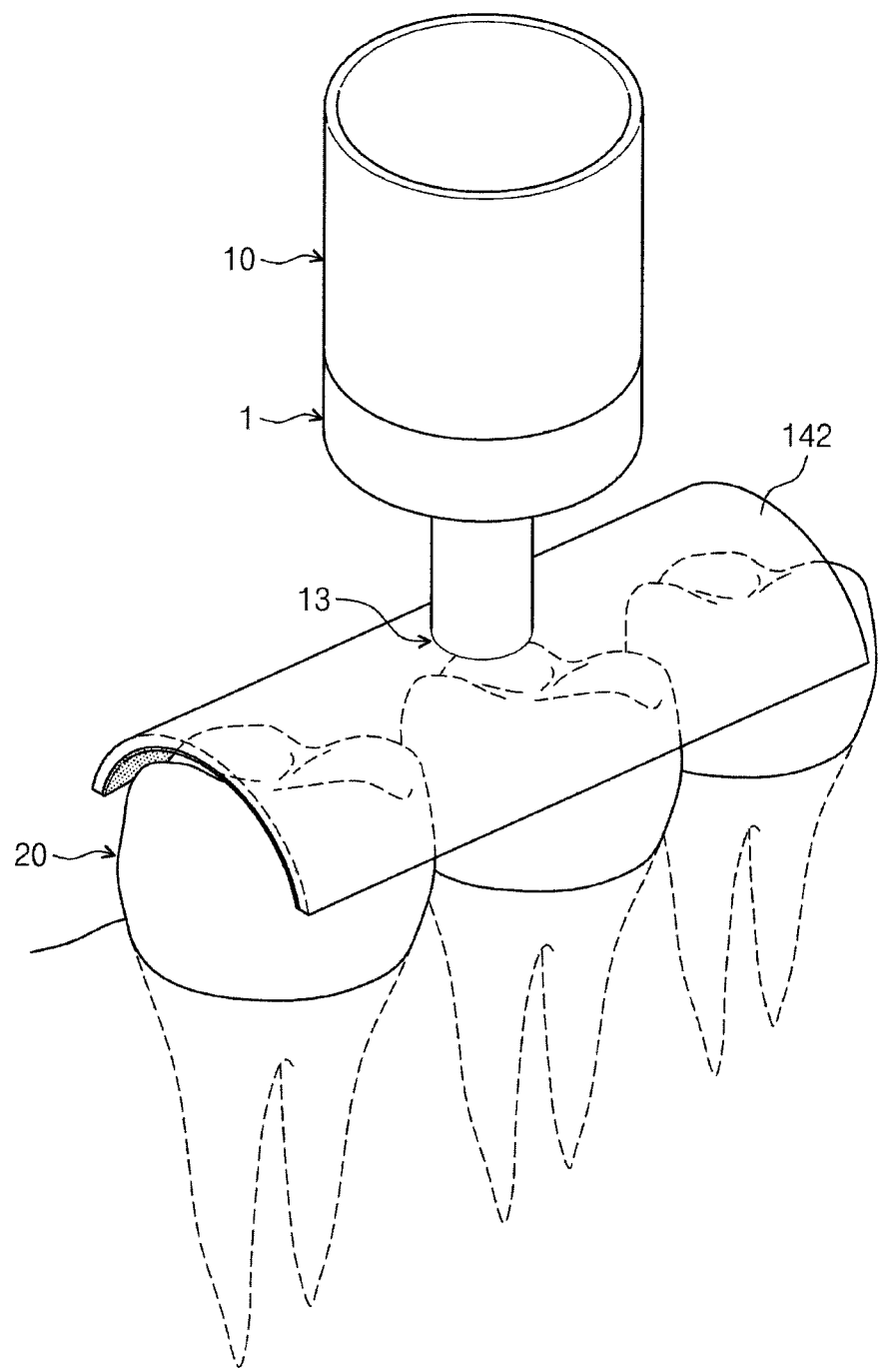
FIG. 17 is an exemplary view illustrating an appearance of treating a tooth by using the plasma enhancement unit provided with a cover according to another embodiment of the inventive concept.

FIG. 17 is an exemplary view illustrating an appearance of treating a tooth 20 by using the plasma enhancement unit 1 provided with the cover 142 according to another embodiment of the inventive concept.

As illustrated in FIG. 17, the user (for example, a medical staff) may supply plasma including an enhancement material M to a tooth 20 while covering the tooth 20 of the patient with the cover 142 to treat the tooth 20 or prevent related diseases by removing various germs (for example, germs that cause dental caries) existing on a surface of the tooth 20.

Figure 18:
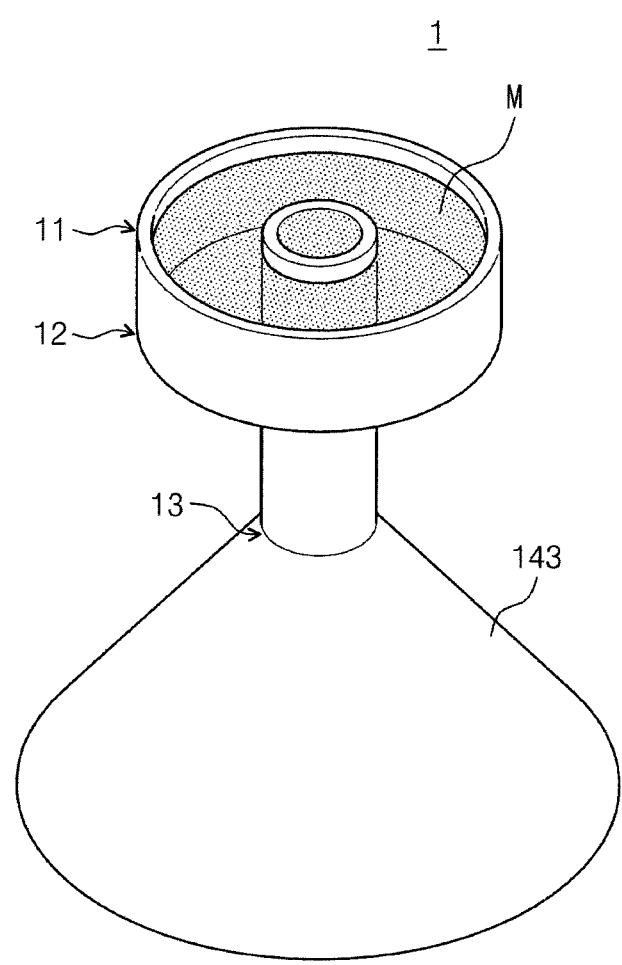
FIGS. 18 and 19 are an exemplary perspective view and a sectional view of the plasma enhancement unit provided with a cover according to another embodiment of the inventive concept.
Figure 19:
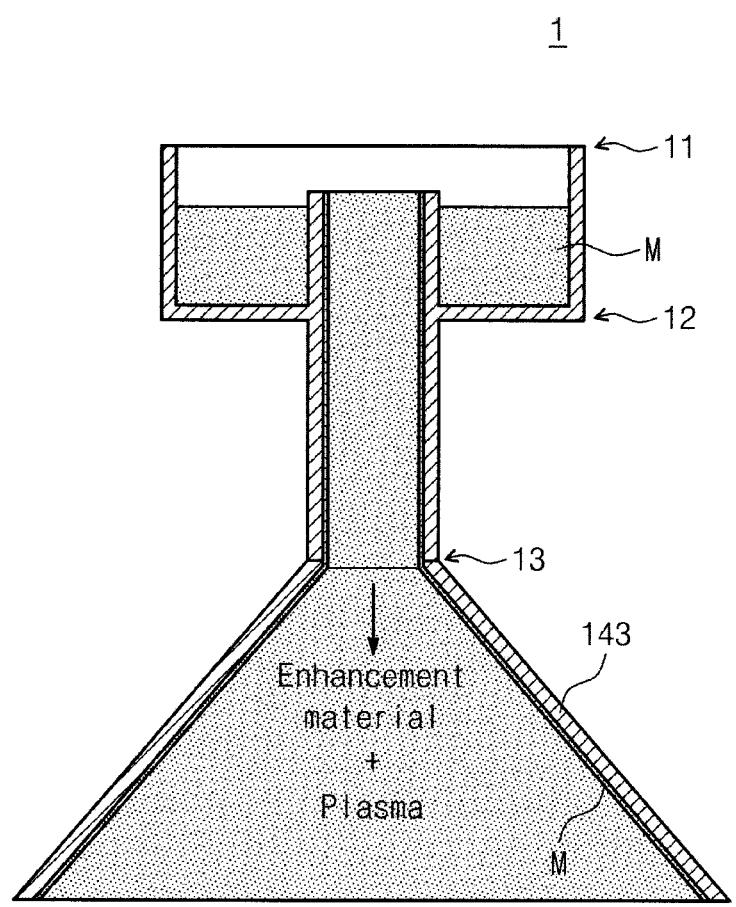

FIGS. 18 and 19 are an exemplary perspective view and a sectional view of the plasma enhancement unit 1 provided with a cover 143 according to another embodiment of the inventive concept.

Unlike the cover 142 having a semi-cylindrical shape, which has been described above with reference to FIGS. 14 to 17, According to another embodiment of the inventive concept, an area of a section of the cover 143, which section is perpendicular to the discharge direction of the plasma, may increase as it goes away from the plasma discharge part 13 of the plasma enhancement unit 1.

For example, as illustrated in FIGS. 18 and 19, the cover 143 may have an appearance in which the shape of the section of the cover 143, which section is perpendicular to the discharge direction of the plasma, is circular, for example, a shape of an overturned funnel.

Figure 20:
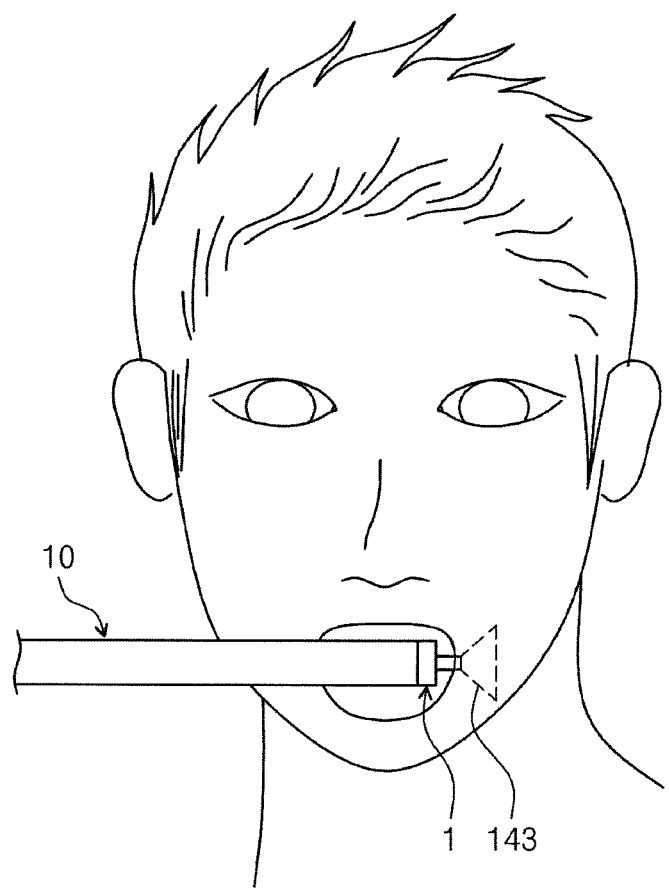
FIG. 20 is an exemplary view illustrating an appearance of treating a mucous membrane by using the plasma enhancement unit 1 provided with the cover 143 according to another embodiment of the inventive concept.

FIG. 20 is an exemplary view illustrating an appearance of treating a mucous membrane by using the plasma enhancement unit 1 provided with the cover 143 according to another embodiment of the inventive concept.

As illustrated in FIG. 20, the user (for example, a medical staff) may supply plasma including an enhancement material M while attaching the cover 143 to an affected area located in a mucous membrane (for example, an inside of a cheek, a palate, or a gum) in a cavity to treat inflammations (for example, cavity inflammations) formed in the mucous membrane or prevent related diseases.

The above-mentioned cover 142 and 143 may surround a space from which the plasma including the enhancement material M is discharged to concentrate the plasma mixed with the enhancement material M on the affected area.

Then, the enhancement material M mixed with the plasma is accommodated in the space R provided in the interior of the plasma enhancement unit 1 or along the delivery path P along which the plasma flows, but according to embodiments, the enhancement material M may be accommodated inside the cover 142 and 143.

For example, as illustrated in FIGS. 14 to 16, the enhancement material M may be applied to an inside of the semi-cylindrical cover 142, and as illustrated in FIG. 19, may be applied on an inside of the funnel-shaped cover 143.

In order to identify a plasma operation enhancing effect according to the plasma enhancement member of the inventive concept, the inventor(s) performed a sterilization experiment and a tooth whitening experiment by plasma as follows.

Figure 21:
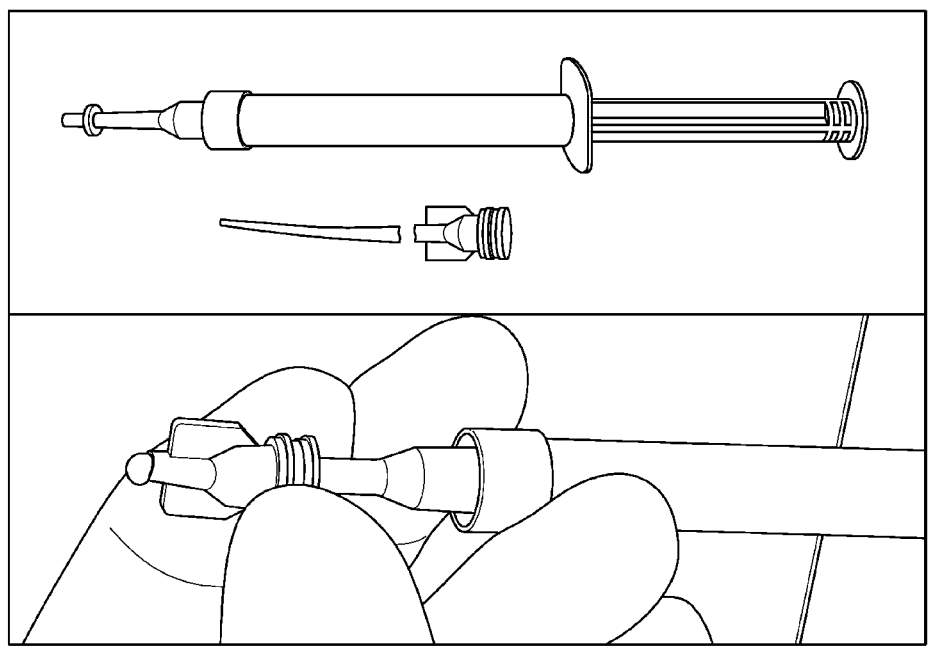
FIG. 21 is an image for explaining a process of providing a plasma enhancement member.
Figure 22:
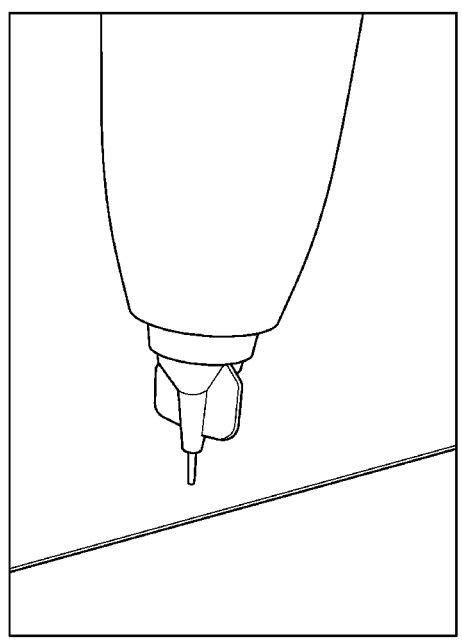
FIG. 22 is an image illustrating an appearance in which the plasma enhancement member is mounted on a nozzle of a plasma generator.
Figure 23:
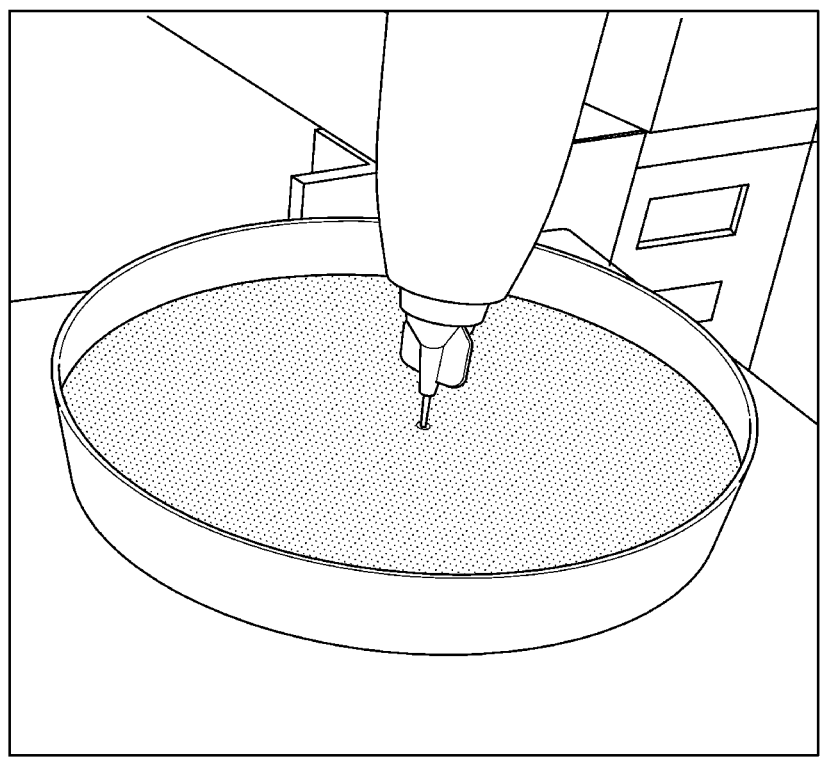
FIG. 23 is an image illustrating an appearance in which plasma is generated by the plasma generator, on which the plasma enhancement member is mounted, and the plasma is irradiated to ta petri dish, in which germs are cultivated.

FIG. 21 is an image for explaining a process of providing a plasma enhancement member. FIG. 22 is an image illustrating an appearance in which the plasma enhancement member is mounted on a nozzle of a plasma generator. FIG. 23 is an image illustrating an appearance in which plasma is generated by the plasma generator, on which the plasma enhancement member is mounted, and the plasma is irradiated to a petri dish, in which germs are cultivated.

First, in order to provide a plasma enhancement member, as illustrated in FIG. 21, an end of a butterfly tip used for treating a tooth was cut away and hydrogen peroxide ($H_2O_2$) of gel type of a concentration of 5.4% was injected to the tip as an enhancement material.

Then, as illustrated in FIG. 22, a tip, into which hydrogen peroxide is injected, was mounted on the nozzle of the plasma generator, and as illustrated in FIG. 23, plasma was ejected to the petri dish, in which *S. Mutans* had been cultivated by operating the plasma generator.

Further, the plasma was ejected to the petri dish, in which *Mutans* had been cultivated, by mounting only a butterfly tip, an end of which is cut away, on the nozzle of the plasma generator as a comparison example of the inventive concept.

Figure 24:
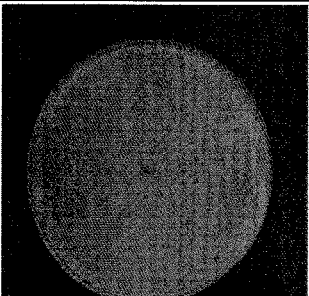
FIG. 24 is an image for identifying sterilization effect of plasmas according to a comparison example in which only a tip is mounted to a nozzle of a plasma generator and an embodiment in which a top, into which hydrogen peroxide is injected, is mounted.
Figure 24:
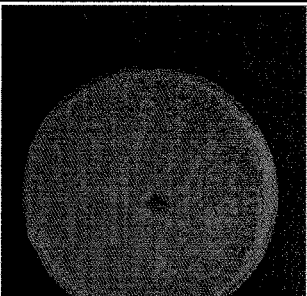
Figure 24:
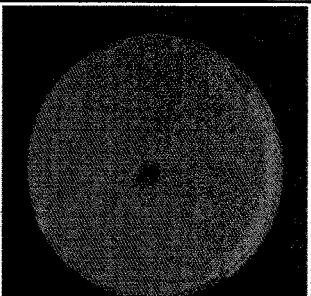
Figure 24:
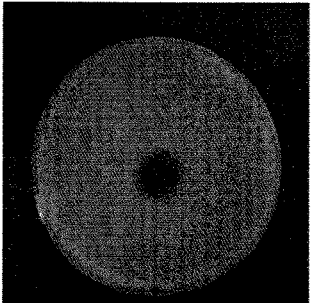
Figure 24:
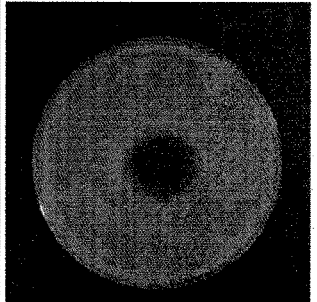
Figure 24:
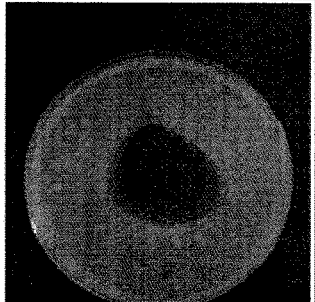

FIG. 24 is an image for identifying sterilization effect of plasmas according to a comparison example in which only a tip is mounted to a nozzle of a plasma generator and an embodiment in which a top, into which hydrogen peroxide is injected, is mounted.

In a sample of the comparison example in which only a tip was mounted to a nozzle and plasma was ejected to a petri dish, in which germs were cultivated, germs were killed in circular areas having diameters of about 0.2 cm, about 0.7 cm, and about 0.9 cm when 15 seconds, 30 seconds, and 60 seconds elapsed.

In a sample of the embodiment in which a tip, into which hydrogen peroxide was injected, was mounted to a nozzle and plasma including hydrogen peroxide was ejected, germs were killed in circular areas having diameters of about 1.8 cm, about 2.8 cm, and about 4.4 cm when 15 seconds, 30 seconds, and 60 seconds elapsed.

The plasma ejection times and the sizes of sterilization areas of the comparison example and the embodiment are as in the following table.

TABLE 1

| | | Plasma ejection time (s) | | |
| --- | --- | --- | --- | --- |
| | | 15 | 30 | 60 |
| Size of sterilization area (cm) | Comparison example | 0.2 | 0.7 | 0.9 |
| | Embodiment | 1.8 | 2.8 | 4.4 |

In the sterilization experimental result, the size of the sterilization area and the sterilization speed were remarkably improved when plasma including hydrogen peroxide was ejected to perform sterilization by using the plasma enhancement member as compared with when only plasma was simply ejected to perform sterilization.

Further, as described above, a tooth whitening experiment was performed by ejecting plasma to a tooth after mounting a tip, into which hydrogen peroxide was injected into a nozzle of a plasma generator. Similarly, a tooth whitening degree was observed after plasma is ejected without a tip being mounted in a comparison example.

In the comparison example and the embodiment, the number of used teeth was 50 and the plasma ejection time was 20 minutes when the tooth whitening experiments were performed.

In order to analyze a whitening degree of a tooth, a change rate ΔE of the brightness of the tooth was calculated after the whitening process was calculated by photographing a darkroom condition by using a stereoscopic microscope before and after the tooth whitening process and obtaining an average of the brightness acquired from several portions of the tooth image by using Photoshop that is an image processing program.

In the comparison result, the average of the change rates ΔE of the brightness of 50 teeth was 2.61, and in the embodiment, the average of the change rates of the brightness of 50 teeth was 7.64, which is 2.93 times as high as that of the comparison example, so that the change rate of the brightness of the teeth was improved.

Figure 25:
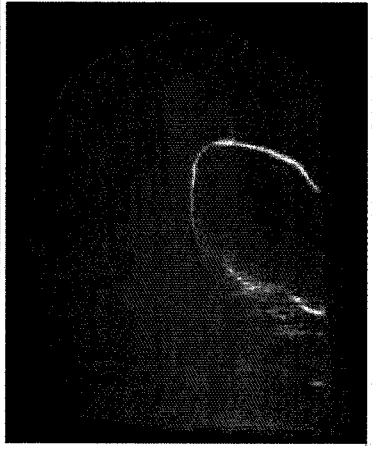
FIG. 25 is an image before and after a whitening process of two teeth, on which a whitening process is performed, according to a comparison example.
Figure 25:
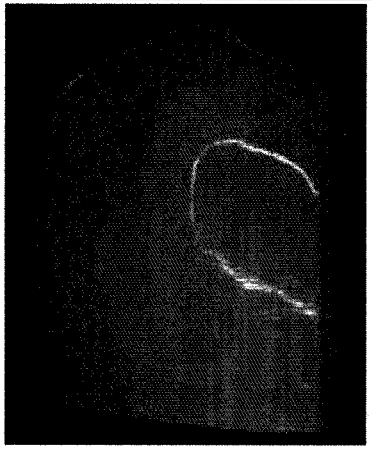
Figure 25:
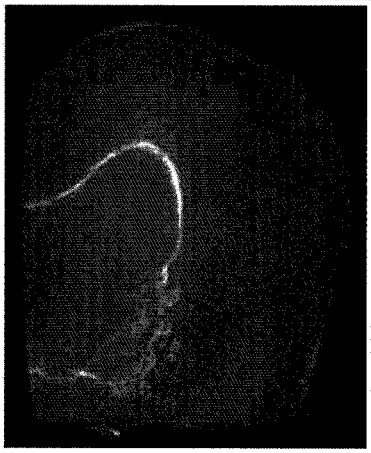
Figure 25:
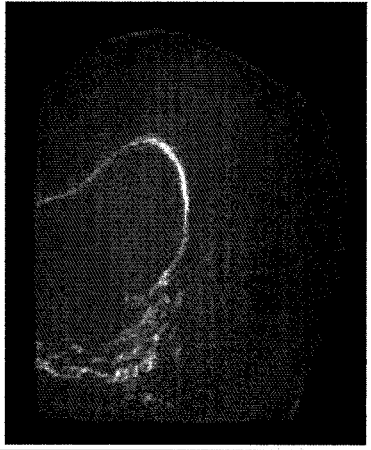
Figure 26:
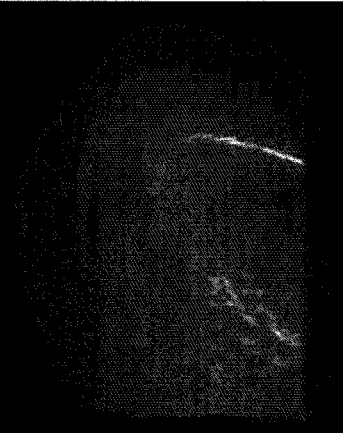
FIG. 26 is an image before and after a whitening process of two teeth, on which a whitening process is performed, according to an embodiment.
Figure 26:
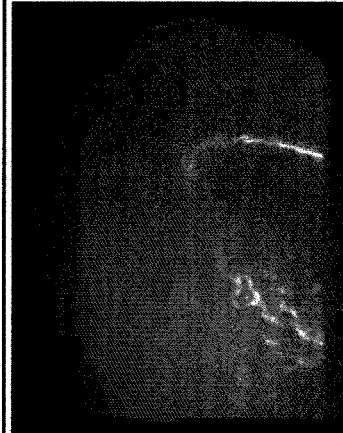
Figure 26:
Figure 26:
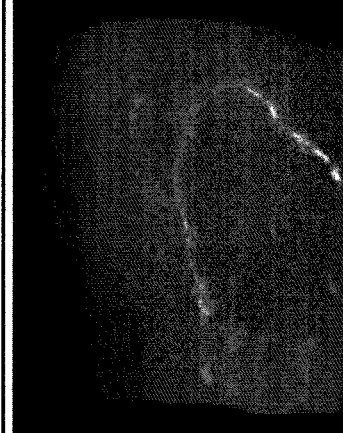

FIG. 25 is an image before and after a whitening process of two teeth (teeth 1 and 2) on which a whitening process is performed according to the comparison example. FIG. 26 is an image before and after a whitening process of two teeth (teeth 3 and 4) on which a whitening process is performed according to the embodiment.

The change rates ΔE of teeth 1 to 4 according to the comparison example and the embodiment are as follows.

TABLE 2

|  | Tooth | Change rate ΔE of brightness |
|---|---|---|
| Comparison example | 1 | 2.62 |
|  | 2 | 2.60 |
| Embodiment | 3 | 7.66 |
|  | 4 | 7.62 |

In the whitening experimental result, it can be seen that the brightness of the teeth of the embodiment in which plasma including hydrogen peroxide by using the plasma enhancement member is ejected to whiten the teeth is higher than the brightness of the teeth of the comparison example in which only plasma is simply ejected to whiten the teeth. In other words, the tooth whitening effect may become about 3 times when the teeth are whitened by using the plasma enhancement member according to the inventive concept as compared with the case in which the teeth are whitened simply by the plasma.

Although the inventive concept has been described through the embodiment, the embodiment is provided simply to describe the spirit of the inventive concept and the inventive concept is not limited thereto. It is noted that those skilled in the art may variously modify the embodiment. The scope of the inventive concept is determined only through analysis of the claims.

What is claimed is:

1. A plasma enhancement member comprising:
a coupling part configured to be coupled to an apparatus for generating plasma;
an enhancement material accommodating part in which plasma is mixed with an enhancement material for enhancing an operation of the plasma, the enhancement material being pre-coated on an inner surface of the enhancement material accommodating part;
a plasma discharge part configured to discharge the plasma including the enhancement material; and
a body interface unit coupled to the plasma discharge part,
wherein the enhancement material accommodating part has a delivery path along which the plasma is delivered from the apparatus for generating plasma to the plasma discharge part,
wherein the enhancement material is pre-coated on an entire inside surface of the delivery path, the delivery path being a pipe formed in an interior of the enhancement material accommodating part and extended from the apparatus for generating plasma to the plasma discharge part,
wherein the body interface unit includes a cover extending from the plasma discharge part to surround a space from which the plasma is discharged,
wherein a section of the cover viewed from a first direction that is perpendicular to a discharge direction of the plasma is curved and a section of the cover viewed from a second direction that is perpendicular to the discharge direction of the plasma and the first direction is straight,
wherein an additional enhancement material is pre-coated on an inner surface of the cover.

2. The plasma enhancement member of claim 1, wherein the coupling part is configured to be coupled to an end of a nozzle of the apparatus for generating plasma.

3. The plasma enhancement member of claim 2, wherein the coupling part is screw-coupled to the nozzle.

4. The plasma enhancement member of claim 3, wherein the coupling part is coupled to a screw formed in the nozzle to have a pitch in a direction that is parallel to an axis of the nozzle.

5. The plasma enhancement member of claim 1, wherein the enhancement material is gel-type hydrogen peroxide.

6. The plasma enhancement member of claim 1, wherein the pipe has a tapered portion and the enhancement material is pre-coated on an entire inside surface of the tapered portion.

7. The plasma enhancement member of claim 1, wherein the pipe has a cylindrical portion and the enhancement material is pre-coated on an entire inside surface of the cylindrical portion.

8. The plasma enhancement member of claim 1, wherein the pipe has a cylindrical portion and at least one tapered portion, and the enhancement material is pre-coated on entire inside surfaces of the cylindrical portion and the at least one tapered portion.

9. A plasma enhancement device comprising:
a plasma generating device having a nozzle discharging plasma; and
a plasma enhancement member coupled to the nozzle of the plasma generating device to receive plasma and enhance operational performance of the plasma,
wherein the plasma enhancement member comprises:
a coupling part coupled to an end of the nozzle of the plasma generating device;
an enhancement material accommodating part in which the plasma is mixed with an enhancement material to enhance the operational performance of the plasma, the enhancement material being pre-coated on an inner surface of the enhancement material accommodating part;
a plasma discharge part configured to discharge the plasma mixed with the enhancement material; and
a body interface unit coupled to the plasma discharge part, wherein the enhancement material accommodating part has a delivery path along which the plasma is delivered from the plasma generating device to the plasma discharge part, wherein the enhancement material is pre-coated on an entire inside surface of the delivery path, the delivery path being a pipe formed in an interior of the enhancement material accommodating part and extended from the plasma generating device to the plasma discharge part, wherein the body interface unit includes a cover extending from the plasma discharge part to surround a space from which the plasma is discharged, wherein a section of the cover viewed from a first direction that is perpendicular to a discharge direction of the plasma is curved and a section of the cover viewed from a second direction that is perpendicular to the discharge direction of the plasma and the first direction is straight, wherein an additional enhancement material is pre-coated on an inner surface of the cover.

10. The plasma enhancement device of claim 9, wherein the enhancement material is gel-type hydrogen peroxide.

* * * * *